US008996130B2

(12) United States Patent
Camps et al.

(10) Patent No.: US 8,996,130 B2
(45) Date of Patent: Mar. 31, 2015

(54) TEMPORARY TOUCH-PROOF CONNECTOR FOR HEARTWIRES

(75) Inventors: Antoine Camps, Gulpen-Wittem (NL); Markus Lazeroms, Vroenhoven-Riemst (BE); Jean Rutten, Bocholtz (NL); Paulus Van Venrooij, Hoensbroek (NL); Bernard Cuisset, Boulogne S/Helpe (FR)

(73) Assignee: Medtronic, Inc., Minneapolis, MN (US)

( * ) Notice: Subject to any disclaimer, the term of this patent is extended or adjusted under 35 U.S.C. 154(b) by 614 days.

(21) Appl. No.: 13/032,835

(22) Filed: Feb. 23, 2011

(65) Prior Publication Data
US 2011/0207352 A1 Aug. 25, 2011

Related U.S. Application Data

(60) Provisional application No. 61/307,173, filed on Feb. 23, 2010.

(51) Int. Cl.
| A61N 1/00 | (2006.01) |
| H01R 24/58 | (2011.01) |
| A61N 1/16 | (2006.01) |
| A61N 1/375 | (2006.01) |
| A61N 1/05 | (2006.01) |
| H01R 13/44 | (2006.01) |
| H01R 13/52 | (2006.01) |

(52) U.S. Cl.
CPC .......... *H01R 24/58* (2013.01); *A61N 1/16* (2013.01); *A61N 1/3752* (2013.01); *A61N 1/0502* (2013.01); *H01R 13/44* (2013.01); *H01R 13/5213* (2013.01); *H01R 2201/12* (2013.01)
USPC ........................................................ 607/116

(58) Field of Classification Search
None
See application file for complete search history.

(56) References Cited

U.S. PATENT DOCUMENTS

| 3,035,583 | A | 5/1962 | Hirsh et al. |
| 3,125,095 | A | 3/1964 | Kaufman et al. |
| 3,244,174 | A | 4/1966 | Wexbey et al. |
| 3,416,533 | A | 12/1968 | Fisher et al. |
| 3,664,347 | A | 5/1972 | Harmjanz |
| 3,949,756 | A | 4/1976 | Ace |
| 4,010,756 | A | 3/1977 | DuMont et al. |
| 4,054,144 | A | 10/1977 | Hoffman et al. |
| 4,338,947 | A | 7/1982 | Williams |
| 4,341,226 | A | 7/1982 | Peters |
| 4,442,840 | A | 4/1984 | Wojciechowicz, Jr. |
| 4,444,207 | A | 4/1984 | Robicsek |
| 4,530,368 | A | 7/1985 | Saulson et al. |
| 4,541,440 | A | 9/1985 | Parsonnet |
| 4,553,554 | A | 11/1985 | Lemole |
| 4,630,617 | A | 12/1986 | Ritter et al. |
| 4,633,880 | A | 1/1987 | Osypka et al. |
| 4,693,258 | A | 9/1987 | Osypka et al. |
| 4,972,833 | A | 11/1990 | Wildon |
| 5,217,027 | A | 6/1993 | Hermens |
| 5,241,957 | A | 9/1993 | Camps et al. |
| 5,314,463 | A | 5/1994 | Camps et al. |
| 5,334,045 | A | 8/1994 | Cappa et al. |
| 5,350,419 | A | 9/1994 | Bendel et al. |
| 5,423,876 | A | 6/1995 | Camps et al. |
| 5,557,210 | A | 9/1996 | Cappa et al. |

(Continued)

Primary Examiner — Brian T Gedeon
Assistant Examiner — Ankit Tejani

(57) ABSTRACT

Temporary touch-proof connectors are disclosed that include an insulating body defining a passageway having an open leading end configured to receive a connector element of a medical lead and an enclosed trailing end shielding the connector element.

22 Claims, 12 Drawing Sheets

(56) References Cited

U.S. PATENT DOCUMENTS

| | | |
|---|---|---|
| 5,679,022 A | 10/1997 | Cappa et al. |
| 5,782,892 A | 7/1998 | Castle et al. |
| 5,792,217 A | 8/1998 | Camps et al. |
| 5,871,528 A | 2/1999 | Camps et al. |
| 5,931,861 A | 8/1999 | Werner et al. |
| 6,343,233 B1 * | 1/2002 | Werner et al. ............ 607/119 |
| 6,397,108 B1 | 5/2002 | Camps et al. |
| 2004/0161968 A1 * | 8/2004 | Cawood et al. ............ 439/521 |
| 2006/0009740 A1 * | 1/2006 | Higgins et al. ............ 604/264 |
| 2006/0148287 A1 * | 7/2006 | Zahnen et al. ............ 439/135 |
| 2006/0271136 A1 * | 11/2006 | Wojciechowicz ............ 607/116 |
| 2007/0050005 A1 * | 3/2007 | Lauro ............ 607/126 |
| 2007/0123913 A1 * | 5/2007 | Beulke et al. ............ 606/138 |
| 2007/0129719 A1 * | 6/2007 | Kendale et al. ............ 606/41 |
| 2009/0125060 A1 * | 5/2009 | Rivard et al. ............ 606/232 |

\* cited by examiner

TEMPORARY TOUCH-PROOF CONNECTOR FOR HEARTWIRES

CROSS-REFERENCE TO RELATED APPLICATION

This application claims the benefit under 35 U.S.C. §119(e) of U.S. Provisional Patent Application Ser. No. 61/307,173 filed on Feb. 23, 2010, which is incorporated herein by reference.

BACKGROUND

The present disclosure relates generally to temporary insulating connectors, also referred to as temporary "touch-proof" connectors for coupling with lead connector elements of medical leads extending percutaneously into a patient's body, and more particularly to temporary touch-proof connectors that shield the lead connector elements from making contact with earth or potentially hazardous voltages when not in use.

Unipolar and bipolar surgically implanted temporary heart wires and temporary leads and nerve, organ, and muscle stimulation leads or wires are well known in the art, some examples of which may be found in the issued U.S. patents listed in Table I below.

TABLE I

| U.S. Pat. No. | Title |
|---|---|
| 3,035,583 | Conductive Sutures |
| 3,125,095 | Flexible Stainless Steel Sutures |
| 3,244,174 | Body Implantable Conductor |
| 3,416,533 | Conductive Catheter |
| 3,664,347 | Electric Heart Stimulation Method and Electrode |
| 3,949,756 | Sutures with Notch Near Needle-Suture Junction |
| 4,010,756 | Heart Pacer Lead Wire with Break-Away Needle |
| 4,054,144 | Short-Crimp Surgical Needle |
| 4,338,947 | Positive Fixation Heart Wire |
| 4,341,226 | Temporary Lead with Insertion Tool |
| 4,442,840 | Electrical Connector Apparatus and Method for a Temporary Cardiac Pacing Wire |
| 4,444,207 | Method of Anchoring a Temporary Cardiac Pacing Lead |
| 4,530,368 | Temporary Bipolar Pacing Lead |
| 4,541,440 | Bipolar Epicardial Temporary Pacing Lead |
| 4,553,554 | Electrical Lead and Method for Temporary Cardiac Pacing |
| 4,630,617 | Heart Pacer Lead Wire with Pull-Away Needle |
| 4,633,880 | Surgical Electrode |
| 4,693,258 | Surgical Electrode for Cardiac Pacing and Monitoring |
| 4,972,833 | Epicardial Pacing Lead |
| 5,217,027 | Temporary Cardiac Lead |
| 5,241,957 | Bipolar Temporary Pacing Lead and Connector and Permanent Bipolar Nerve Wire |
| 5,314,463 | Bipolar Nerve Electrode |
| 5,334,045 | Universal Cable Connector for Temporarily Connecting Implantable Leads and Implantable Medical Devices with a Non-Implantable System Analyzer |
| 5,350,419 | Cardiac Pacing Lead |
| 5,423,876 | Intramuscular Lead Having Improved Insertion |
| 5,557,210 | Universal Cable Connector for Temporarily Connecting Implantable Stimulation Leads and Implantable Medical Devices with a Non-Implantable System Analyzer |
| 5,679,022 | Universal Cable Connector for Temporarily Connecting Implantable Stimulation Leads and Implantable Medical Devices with a Non-Implantable System Analyzer |
| 5,782,892 | Medical Lead Adaptor for External Medical Device |
| 5,792,217 | Temporary Bipolar Heart Wire |
| 5,871,528 | Temporary Bipolar Heart Wire |
| 5,931,861 | Medical Lead Adaptor Having Rotatable Locking Clip Mechanism |
| 6,397,108 | Safety Adaptor for Temporary Medical Leads |

All patents listed in Table I are hereby incorporated by reference herein in their respective entireties. Certain of the patents listed in Table I disclose surgically implanted temporary heart wires or leads for use with an external unipolar or bipolar cardiac pacemaker and/or monitor or pacing system analyzer (PSA) in a manner that is well known in the medical field. As described further below, temporary heart wires are implanted in a patient's body to extend between a heart chamber through a percutaneous incision to an external medical device and are removed after a time. Heart wires are sometimes alternatively referred to as temporary pacing leads but are distinguished from endocardial temporary pacing leads that are passed percutaneously through an incision into a vein and transvenously advanced into a heart chamber, typically employing a removable stiffening stylet, as disclosed in the above-referenced, commonly assigned '861 and '892 patents. Such endocardial temporary pacing leads are implanted and used for closed-chest temporary pacing and monitoring of a patient's heart in a variety of single and dual chamber pacing modes. When their use is terminated, they are retracted through the transvenous route, and the incision is closed.

Unipolar heart wires, e.g., the Medtronic® Model 6491, Model 6492, Model 6494, and Model 6500 Temporary Pacing Leads, and bipolar heart wires, e.g., the Medtronic® Model 6495 (J-2M) Temporary Pacing Lead, are shown in the above-referenced, commonly assigned '463, '217 and '328 patents. Such unipolar and bipolar heart wires are implanted in the course, preferably at the end, of a surgical procedure where the heart is surgically exposed, e.g., to provide post-surgical temporary pacing and monitoring, and are withdrawn through a percutaneous incision by applied traction when their use is to be terminated.

The elongated unipolar and bipolar heart wire bodies are constructed of a single conductor or two conductors, each conductor comprising a number of fine, stainless steel wires twisted together to form a single, flexible, multifilament wire. The major portion of each such conductor within the wire body is typically insulated with a polyethylene, polytetrafluoroethylene, silicone, nylon, or other suitable electrically non-conductive and bio-compatible materials to insulate the wires from one another (in bipolar versions) and from the environment. A short length of each such conductor at the distal end of the heart wire body is exposed to act as a pace/sense electrode when passed into the myocardium. The distal end of the most distal electrode is axially coupled to an elongated retention coil that in turn is coupled axially by a severable, non-conductive, filament to a fine, curved surgical needle.

The fixation into the myocardium is accomplished with the heart exposed by using the curved needle to pierce the epicardium and to draw the pace/sense electrode(s) and retention coil through a portion of the myocardium without penetrating all the way through the myocardium and into a heart chamber or blood vessel. In this process, the needle is passed back out through the epicardium, and the filament coupling the needle with the fixation coil is severed after electrical testing is completed.

A tubular lead connector element is formed at the proximal end of the heart wire body and electrically connected to each insulated wire in an in-line configuration. A straight, Keith-type, cutting needle extends proximally from the proximal end of the most proximal lead connector element and is used to pierce the thoracic wall to extend the proximal portion of the heart wire body outside the body when the surgical incision accessing the heart is closed. Then, the Keith-type needle is typically clipped or broken off, and each heart wire connector element is coupled to an external medical device.

A similar nerve stimulation wire and procedure of implantation is disclosed in the above-referenced, commonly assigned, '463, '217 and '328 patents.

The proximal connector elements of such temporary endocardial pacing leads and heart wires are typically coupled to terminals of external pacemaker pulse generators, e.g., the Medtronic® Model 5348 and 5388 single chamber or dual chamber pacemaker pulse generators or similar devices which are available on the market. Other suitable connections are also considered, for example if the lead length is short, by using an extension cable which terminates in the external pacemaker pulse generator. A direct connection may be made if the lead or wire connector elements are compatible with the external medical device connector terminals and if the lead or wire body is long enough. In certain situations, the connector elements are not coupled to terminals of pulse generators and thus the pacing leads and heart wires are coiled up and positioned for future use, for example by being taped to a patient's chest. When not coupled to terminals of a pulse generator, temporary touch-proof connectors are used so as to prevent connector elements from contacting earth or hazardous voltages.

Concerns relating to the safety of leaving any lead connector element exposed have been voiced by regulatory agencies over many years. It is dangerous to a patient to conduct electrical current or static electricity through a lead into a patient's body, particularly through a temporary pacing lead or heart wire attached to the heart. Connector regulations IEC 60601-1 dictate that medical leads shall be constructed in such a way that no conductive part or surface of a connector element in the part of the medical lead remote from the patient can contact earth or possibly hazardous voltages. Moreover, regulations IEC 60601-1 and 60601-2-31 including amendment 1 requires connections to a patient be equipped with touch-proof connectors that can only be implemented by industrial manufacturing.

SUMMARY

Temporary touch-proof connectors are disclosed that include an insulating body defining a passageway having an open leading end sized to receive a connector element of a medical lead and an enclosed trailing end shielding the connector element. The passageway can transition from a first, open configuration to a second, closed configuration. In the open configuration, a shape of the passageway is altered to receive a connector element of a lead. In the closed configuration, the shape of the passageway is altered to secure the connector element therein.

BRIEF DESCRIPTION OF THE DRAWINGS

Features discussed herein will be appreciated as the same becomes better understood by reference to the following detailed description when considered in connection with the accompanying drawings, in which like numbered reference numbers designate like parts throughout the figures thereof, and wherein.

DETAILED DESCRIPTION

Figure 1:
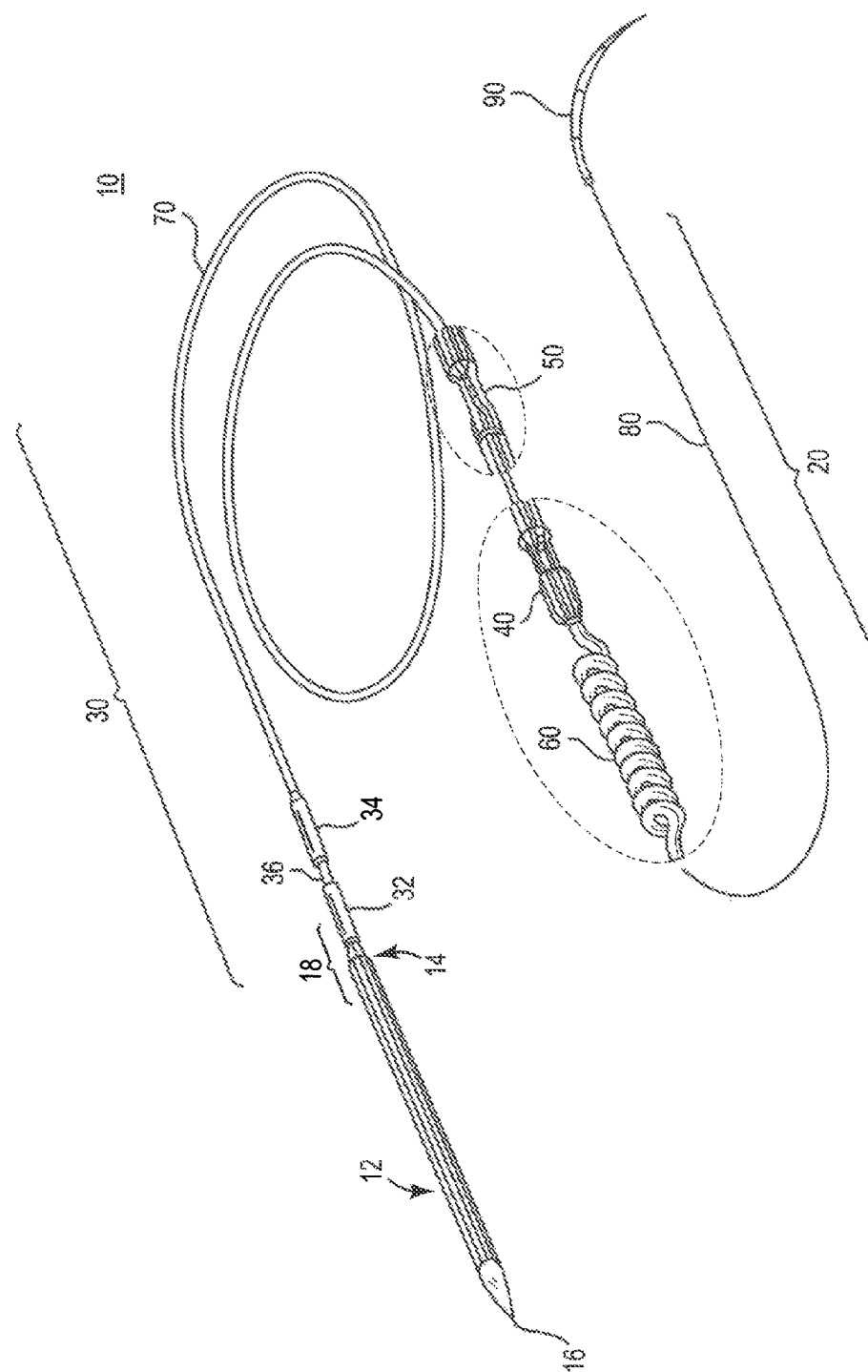
FIG. 1 is a perspective view of a typical bipolar temporary medical lead heart wire that may be advantageously used with a temporary touch-proof connector.

The various embodiments of touch-proof connectors described herein may be employed to reliably attach with and fully enclose the connector element(s) located outside a patient's body of a temporary medical lead that extends percutaneously through the patient's skin so as to shield and insulate the connector element(s). The temporary medical lead and the external medical device includes those used for nerve, muscle, brain or cardiac stimulation and/or monitoring. In this regard, the following terms have the particular meanings and definitions applicable to the specification and claims as set forth below.

The term "temporary medical lead" and any substantially similar variants thereof means an electrical signal and/or stimulation energy conducting lead that has a proximal end having at least one lead connector element and a break-away needle attached thereto, an elongated lead body, and one or more electrode in a distal end section of the lead body. The electrode(s) is adapted to be implanted at a monitoring and/or stimulation site in a patient's body while the lead body extends through the patient's skin, and the lead connector element is adapted to be coupled with a temporary touch-proof connector.

The terms "temporary heart wire", "temporary heart lead" and any substantially similar variants thereof mean a temporary medical lead introduced surgically through the epicardium into the myocardium from the exterior of the heart, where the lead or wire has at least one electrode near its distal end for monitoring, pacing or defibrillating the heart at or near a myocardial or epicardial site, and where the lead or wire has at least one connector element coupled with the break-away needle at its proximal end for electrical connection to an external pacing, monitoring, or defibrillating apparatus. "The terms "heart wire," "heart lead" and any substantially similar variants thereof are synonymous.

The term "proximal" means that portion of an apparatus, or component or element of an apparatus, disposed in closer proximity to the end of the temporary medical lead remaining outside a patient's body following the lead implantation procedure than it is to the distal end of the heart wire implanted in the patient's body.

The term "distal" means that portion of an apparatus, or component or element of an apparatus, disposed in closer proximity to the end of the temporary medical lead that is implanted in the patient's body, e.g., the distal electrodes and retention coil of a heart wire in the myocardium, than it is to the proximal end that remains outside the patient's body following the lead implantation procedure.

For simplicity of illustration, the temporary touch-proof connector embodiments are disclosed in detail in relation to use with temporary heart wires or nerve stimulation wires having bipolar, in-line connector elements attached to the proximally extending break-away needle. As will be apparent, the temporary touch-proof connector embodiments can be employed with temporary unipolar or bipolar heart wires or nerve stimulation wires having only a single connector element attached to the proximally extending break-away needle. Similarly, the temporary touch-proof connector embodiments can be modified to be employed with temporary multi-polar heart wires or nerve, organ or muscle stimulation and monitoring wires having more than two in-line connector elements attached to the proximally extending break-away needle.

FIG. 1 shows a perspective view of an embodiment of a bipolar, in-line, heart wire usable with a temporary touch-proof connector designed specifically for pacing and sensing applications, e.g., the above listed Medtronic® Model 6495 Temporary Pacing Lead. Suitable unipolar and bipolar, heart and nerve, wires are disclosed in greater detail in the above-referenced, commonly assigned '226 and '957 patents, respectively. Other features of the particular temporary medical each used with the temporary touch-proof connectors described herein may take other forms than those depicted in FIG. 1.

Temporary medical lead or wire 10 preferably comprises break-away percutaneous penetrating needle 12, weakened zone 18, a proximal end segment 30 comprising proximal and distal lead connector elements 32 and 34, elongated lead body 70 enclosing first and second conductors, a distal end segment comprising proximal electrode 50, distal electrode 40, retention coil 60, and strand 80, and an atraumatic curved needle 90. It should be noted that the proximal lead connector element 32 may in fact be formed of a distal portion of the break-away needle shaft distal to the weakened zone 18 as shown in the '957 patent. The temporary touch-proof connector embodiments discussed herein enclose at least a portion of the proximal end segment 30, and in particular connector elements 32 and 34.

Strand 80, preferably formed of polypropylene and constituting a monofilament, forms retention coil 60, attaches to distal electrode 40 and extends to atraumatic curved needle 90. Retention coil 60 ensures secure temporary fixation of the distal electrodes of heart wire 10 in the heart and prevents dislodgment which might otherwise occur were a straight tipped lead employed. Most preferably, one length of polypropylene comprises coil 60 and strand 80. More than one curved needle 90 may be attached to distal end segment 20 of lead 10. For example, the lead body 70 may be bifurcated in distal end segment 20 such that each conductor of lead body 70 terminates in a separate pace/sense electrode, retention coil, and curved needle attached thereto.

Lead body 70 most preferably comprises conductors that provide a high degree of flexibility and superior mechanical and electrical properties. Lead body 70 may comprise any pair of suitable flexible electrical conductors, such as coaxial conductors or so-called "lamp cord" or "zip-cord" (e.g., side-by-side) conductors. Most preferably, lead body 70 is a coaxial pair of inner and outer electrical conductors, where the conductors are formed of helically wound strands of multifilament or twisted stainless steel. As discussed above, lead body 70 is insulated with a polyethylene, polytetrafluoroethylene, silicone, nylon, or other suitable electrically non-conductive and bi-compatible materials to insulate wires from one another and from the environment.

Electrodes 40 and 50 are preferably formed of medical grade stainless steel suitable for temporary applications, and are preferably spaced a predetermined distance apart known to optimize the delivery of pacing pulses or the detection and sensing of cardiac electrical signals. Distal electrode 40 is mechanically and electrically connected through the inner conductor (not shown in FIG. 1) to proximal connector element 32 at the proximal end of lead 10, which, in turn, is mechanically connected to blunt end 14 of needle 12 by weakened zone 18. Proximal electrode 50 is mechanically and electrically connected through the outer conductor (not shown in FIG. 1) to distal connector element 34. Distal connector element 34 is located distally along proximal end segment 30 from the proximal connector element 32 and spaced therefrom by insulated inner conductor segment 36.

In-line connector elements 32 and 34 are preferably formed of cylindrically shaped, conductive metal rings that are each electrically connected to a conductor of the lead body 70 and have a circular cross-section and diameter substantially equal to or slightly larger than the diameter of lead body 70. Other structural configurations of connector elements 32 and 34 can be employed with the temporary touch-proof connectors described herein and include, but are not limited to, pin-shaped connectors having rectangular or square cross-sections, reed-shaped connectors, and flexible connectors.

Needle 12, most preferably of the atraumatic type, is a break-away Keith-type needle for piercing the thorax, and has pointed end 16 and blunt end 14. Needle 12 is preferably substantially straight between pointed end 16 and blunt end 14. Pointed end 16 has a cutting edge designed for piercing the thoracic wall of the patient. Preferably, the weakened zone 18 separates the proximal end of proximal connector element 32 from blunt end 14. Or, the proximal connector element 32 may be the part of the break-away needle shaft distal to the weakened zone 18. The weakened zone 18 typically is a narrowed section or a heat treated junction of the needle shaft and the proximal end of the proximal connector element 18.

FIG. 1 shows exemplary features of a temporary medical lead 10 that may be connected to a temporary touch-proof connector, as discussed below, wherein the temporary medical lead 10 includes at least one connector element (e.g., connector element 32) extending proximally from the proximal lead segment 30 that is intended to be positioned in an elongated passageway of the temporary touch-proof connector. The passageway is positioned within an insulating body of the temporary touch-proof connector. The insulating body is formed of an electrically non-conductive insulating material such as silicone rubber, polyethylene or polypropylene. The passageway includes an open, leading end and an enclosed, trailing end, which terminates within the insulating body so as to fully enclose a connector element therein.

In relation to FIG. 1, a length of the passageway from the leading end of the passageway to the trailing end of the passageway is formed to encompass an entirety of connector elements 32 and 34, extending to a point of connection between connector element 34 and lead body 70. The insulating body is configured to secure the connector element of the lead within the passageway such that the connector element will be reliably secure within the temporary touch-proof connector and not easily released from the passageway such that the connector element would be undesirably exteriorly exposed. In some embodiments, the passageway of the temporary touch-proof connector transitions from a first, open configuration to a second, closed configuration. In the open configuration, the passageway is configured so that a user can easily insert and remove the connector element from the passageway. In the closed configuration, the connector element is reliably secured within the passageway. In some embodiments, the insulating body is biased in the closed configuration. In this case, an external force (e.g., provided by a hand of a user) is used to alter a shape of the passageway, thus actuating the connectors to the open configuration. Upon release of the force, the connector returns to the closed configuration.

In addition to serving as a device to prevent undesired electrical current or static electricity from passing through a lead to a patient's body during use of the lead, embodiments of the temporary touch proof connectors disclosed herein can also serve as a carrier for leads during packaging and distribution. As leads come into contact with a patient's body during use, it is important that the leads are maintained in sterile packaging prior to use. In some instances, needles (e.g., needle 12 and/or needle 90) can inadvertently puncture or tear the sterile packaging during distribution (e.g., shipping) of the lead. In such a case, the lead must be discarded or re-sterilized. When used as a packaging carrier, the temporary touch-proof connectors described herein can secure and protect needles of the leads from puncturing or tearing the lead packaging.

Figure 2A:
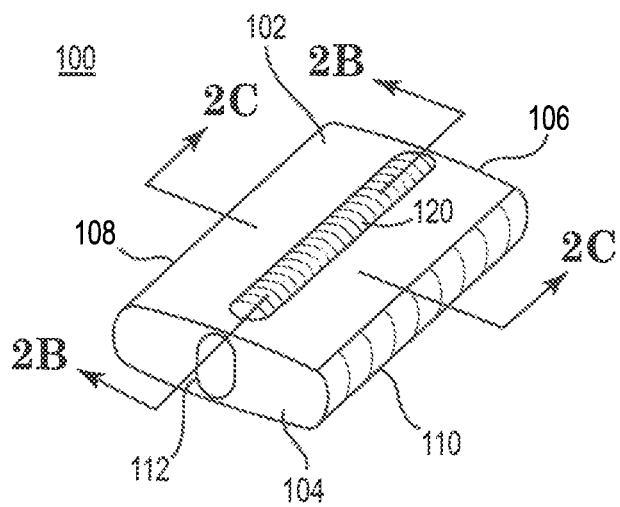
FIGS. 2A-2E illustrate various views of a first embodiment of a temporary touch-proof connector.
Figure 2C:
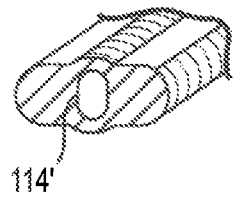
Figure 2D:
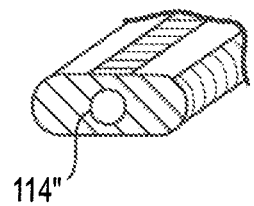
Figure 2E:
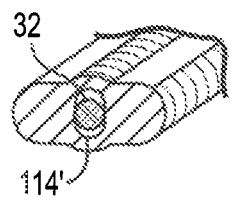
Figure 2B:
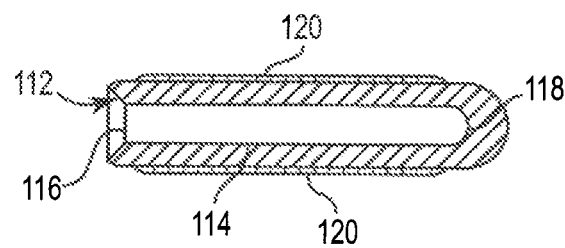

FIGS. 2A-2E illustrate a temporary touch-proof connector 100 for coupling with lead 10 of FIG. 1, and in particular with connector elements 32 and 34. Connector element 32 is schematically shown in FIG. 2E, for reference. Connector 100 includes an elongated, generally rectangular insulating body 102 defining a first or leading end 104 and an opposed, second end 106. Additionally, body 102 includes a first side 108 and an opposed, second side 110 between the first end 104 and the second end 106. Connector 100 is formed to be biased to a closed configuration, such that absent an external force, a connector element disposed therein will be secured within the connector 100. As discussed below, insulating body 102 can be actuated from the closed configuration (as shown in FIG. 2C) to an open configuration (as shown in FIG. 2D) by a user exerting force on sides 108 and 110.

Leading end 104 defines an opening 112 for receiving a connector element. Opening 112 is open to an elongated passageway 114 (FIG. 2B) that includes a leading end 116 receiving a connector element and terminates at a trailing end 118 so as to fully enclose the connector element. Connector 100 is operable between the open configuration and the closed configuration in order to selectively receive and secure the connector element within passageway 114. In particular, insulating body 102 is formed so as to be biased to the closed configuration, wherein a cross-section of passageway 114 is in a generally elliptical shape, shown in FIG. 2C as configuration 114' of passageway 114. In the open configuration, passageway 114 becomes generally circular in shape so as to accept a connector element, shown in FIG. 2D as configuration 114". For example, a user may compress connector 100 between sides 108 and 110 to actuate passageway 114 to the open configuration 114". A user then inserts the connector element into connector 100 and releases compression from the sides 108, 110 so as to secure the connector element 32 within passageway 114, as shown in FIG. 2E, where passageway 114 has returned to configuration 114'.

In configuration 114', passageway 114 includes a minor axis that is sized to be smaller than a diameter of connector element 32. By compressing sides 108 and 110, the minor axis size increases to a size greater than the diameter of connector element 32, allowing the connector element 32 to be easily inserted into passageway 114. After releasing compression from sides 108 and 110, the minor axis is biased to return to the smaller size and thus securing connector element 32 therein. In one embodiment, raised ridges 120 are disposed on top and bottom surface of connector body 102 so as to form the elliptical shape of passageway 114 and aid in changing the shape of passageway 114 when connector body 102 is compressed between sides 108 and 110.

Figure 3A:
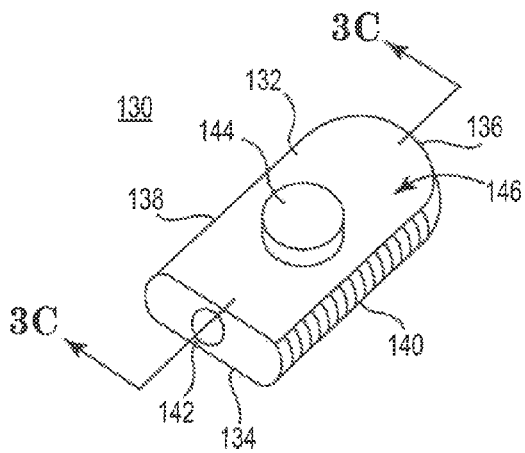
FIGS. 3A-3F illustrate various views of a second embodiment of a temporary touch-proof connector.
Figure 3B:
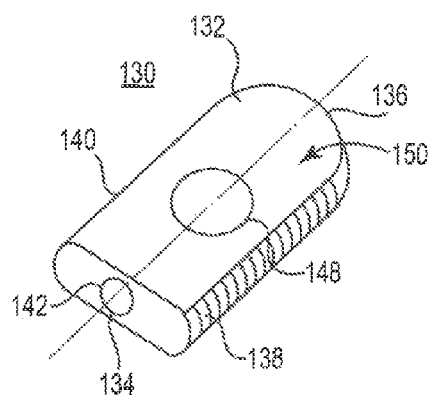
Figure 3C:
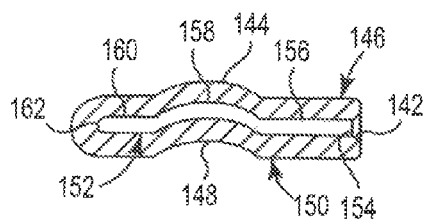
Figure 3D:
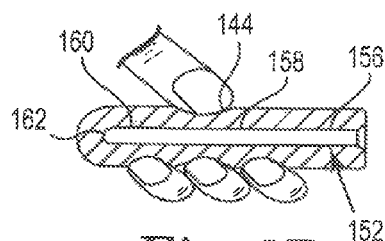
Figure 3E:

FIGS. 3A-3F illustrate a temporary touch-proof connector 130 formed of an elongated insulating body 132 having a first end 134, a second end 136 and opposed sides 138 and 140. First end 134 includes an opening 142 sized to receive a connector element 32. Additionally, connector 130 comprises a push button 144 formed on a top surface 146 of elongated body 132 and a corresponding dimple 148 formed on a bottom surface 150 of elongated body 132. As discussed below, insulating body 132 can be transitioned from a closed configuration, as illustrated in FIG. 3C, to an open configuration as illustrated in FIG. 3D, by depressing push button 144.

Figure 3F:
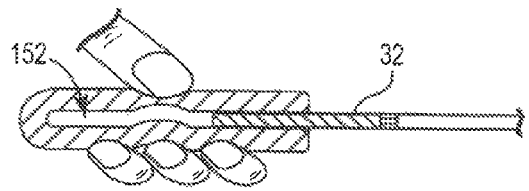

With reference to FIG. 3C, opening 142 is open to an internal passageway 152 that includes an open leading end 154, a leading straight segment 156, an intermediate arcuate segment 158 and a trailing straight segment 160 that terminates at an enclosed trailing end 162. In order to insert a connector element within connector 130, button 144 is depressed by a user (FIG. 3D) such that intermediate segment 158 is generally aligned with leading segment 156 and trailing segment 160. As such, a shape of passageway 152 is altered to be generally straight. The connector element 32 is then inserted (FIG. 3E) so as to be enclosed by trailing end 162. Push button 144 is released to secure connector element 32 within connector 130 such that intermediate segment 158 is biased to secure the connector element 32 within passageway 154. To release connector element 32, button 144 is again depressed so as to generally align segment 158 with segments 156 and 160, as shown in FIG. 3F. A pulling force can then be used to remove connector element 32 from passageway 152.

Figure 4A:
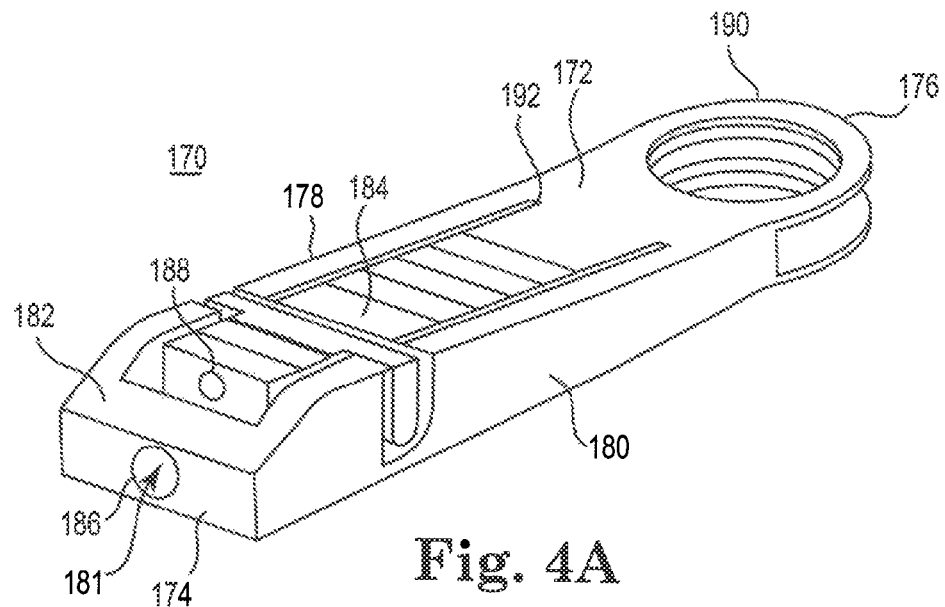
FIGS. 4A-4D illustrate various views of a third embodiment of a temporary touch-proof connector.
Figure 4B:
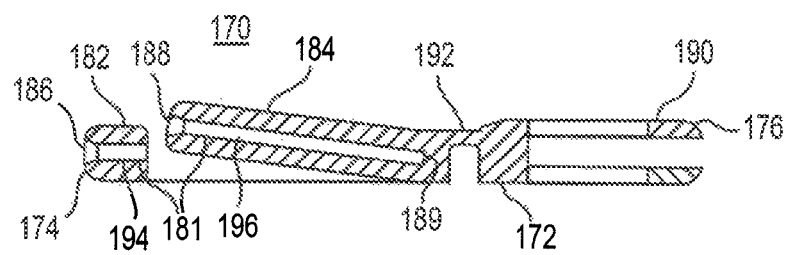
Figure 4C:
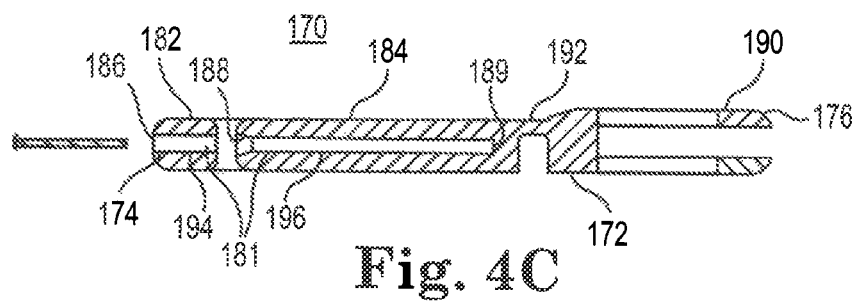

FIGS. 4A-4D illustrate a temporary touch-proof connector 170 formed of an insulating body 172 including a first end 174, a second end 176, and opposed first and second sides 178 and 180. Insulating body 172 also includes a passageway 181, a receiving portion 182 and a locking portion 184 movable with respect to the receiving portion 182. In particular, receiving portion 182 includes an opening 186 to passageway 181 and locking portion 184 includes an opening 188. Passageway 181 terminates at an enclosed, trailing end 189. Locking portion 184 is pivotally coupled to an end portion 190 of connector body 172 through a flexing portion (e.g., a hinge) 192 such that locking portion 184 can rotate with respect to receiving portion 182. As discussed below, passageway 181 can be actuated from a closed configuration, as shown in FIG. 4B, to an open configuration, as shown in FIG. 4C, by depressing locking portion 184 such that openings 186 and 188 are generally aligned.

Figure 4D:
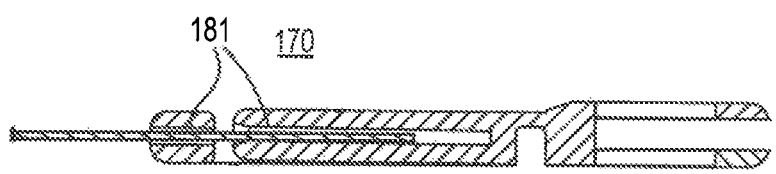

Passageway 181 is formed of a first passageway segment 194 and a second passageway segment 196. Receiving portion 182 maintains first passageway segment 194 and locking portion maintains second passageway segment 196. During use, locking portion 184 is depressed such that first passageway segment 194 is aligned with second passageway segment 196 (as shown in FIG. 4C). Next, a connector element is inserted through the passageway segments 194 and 196 and locking portion 184 is released to secure the connector element within connector 170, as shown in FIG. 4D, wherein locking portion 184 is biased to place a force on the connector element.

Figure 5A:
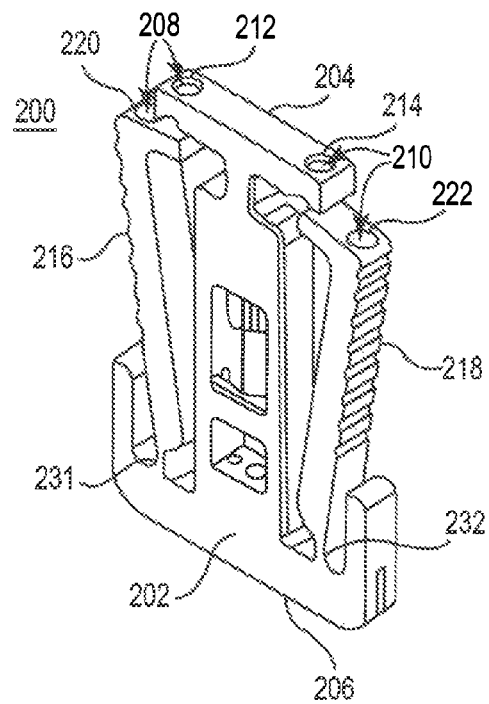
FIGS. 5A-5D illustrate various views of a fourth embodiment of a temporary touch-proof connector.
Figure 5B:
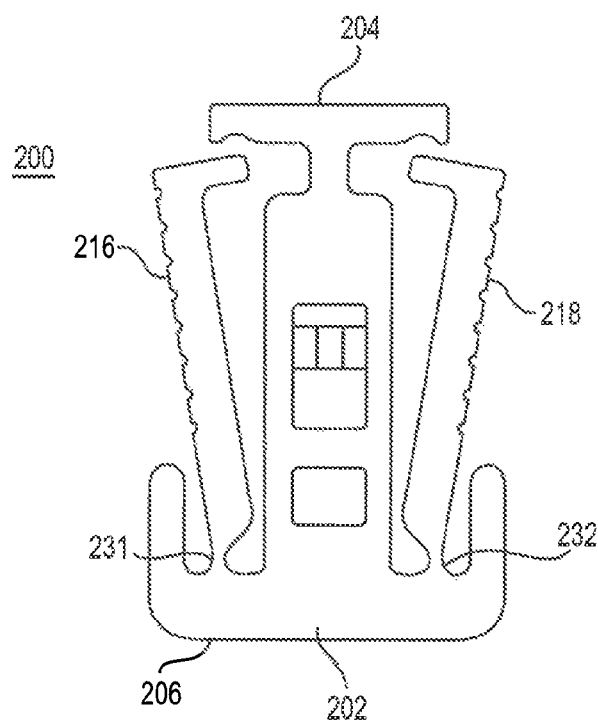
Figure 5C:
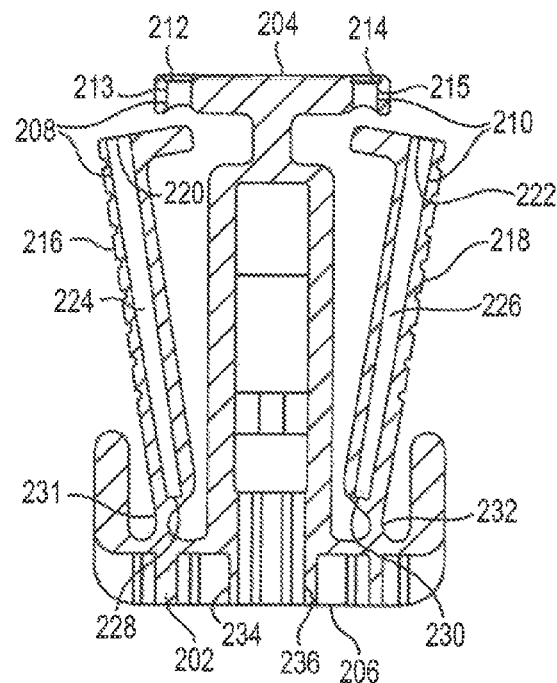
Figure 5D:
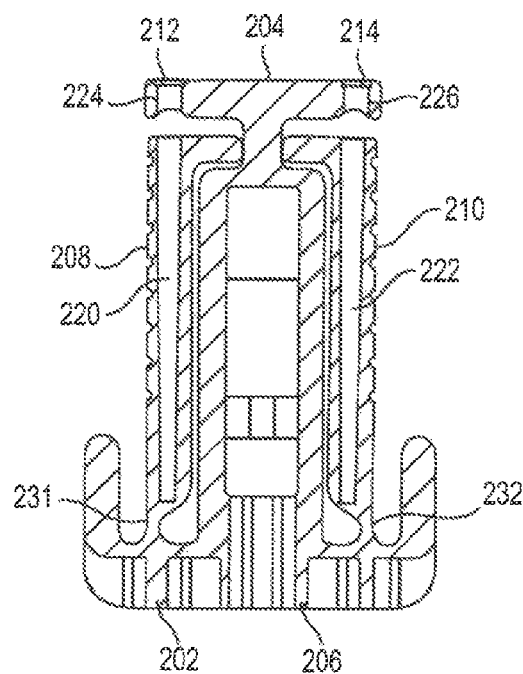

FIGS. 5A-5D illustrate a temporary touch-proof connector 200 formed of a connector body 202 having a first end 204, a second end 206 and first and second passageways 208 and 210. First end 204 includes a first opening 212 leading to a passageway segment 213 of passageway 208 and a second opening 214 leading to a passageway segment 215 of passageway 210. Furthermore, connector 200 includes locking portions 216 and 218 that include corresponding openings 220 and 222 that lead to passageway segments 224 and 226, respectively. Passageways 208 and 210 terminate at closed ends 228 and 230, respectively. Locking portions 216 and 218 are pivotally coupled to connector body 202 through flexing portions 231 and 232, respectively. During use, locking portions 208 and 210 are compressed (i.e., pushed together toward each other) such that passageway segments 224 and 226 are generally aligned with openings 212 and 214, respectively, as shown in FIG. 5D. Once aligned, connector elements can be inserted through openings 212 and 214 and into passageway segments 224 and 226. As a result, multiple connector elements can be positioned within connector 200. When used as a carrier during packing and distribution, connector 200 includes internal passageways 234 and 236 that are configured to receive needles (e.g., needle 12) therein. As such, the needles will be protected during packaging and distribution.

Figure 6A:
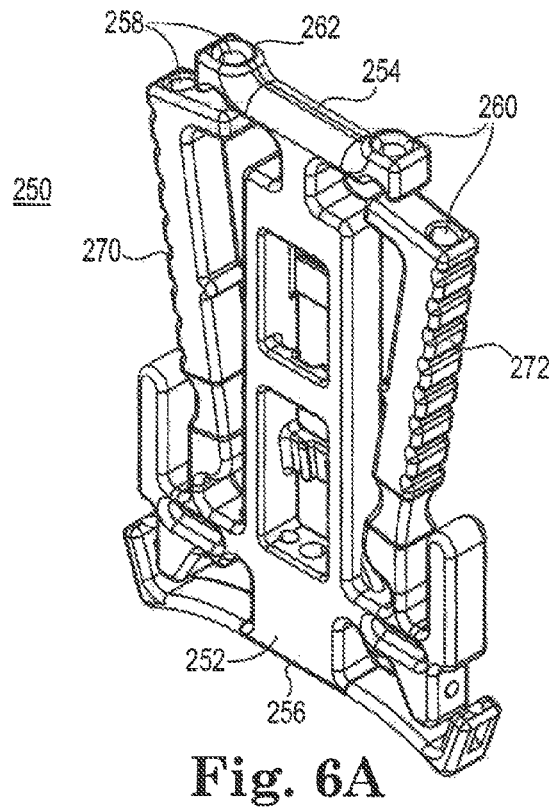
FIGS. 6A-6E illustrate various views of a fifth embodiment of a temporary touch-proof connector.
Figure 6B:
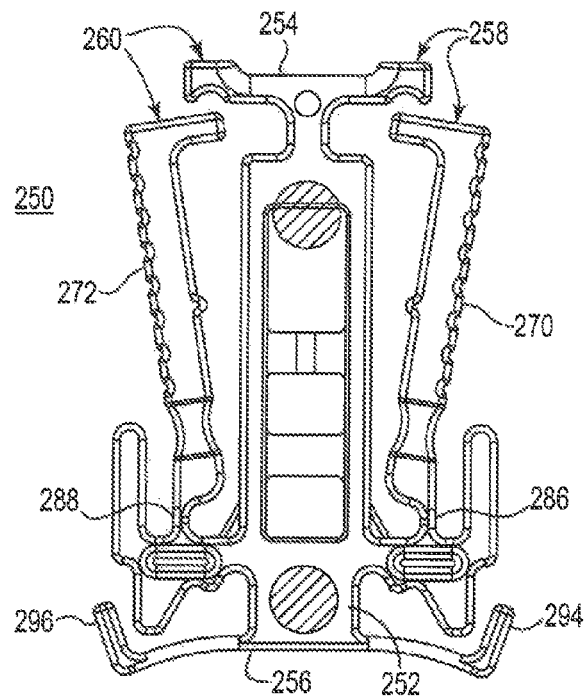
Figure 6C:
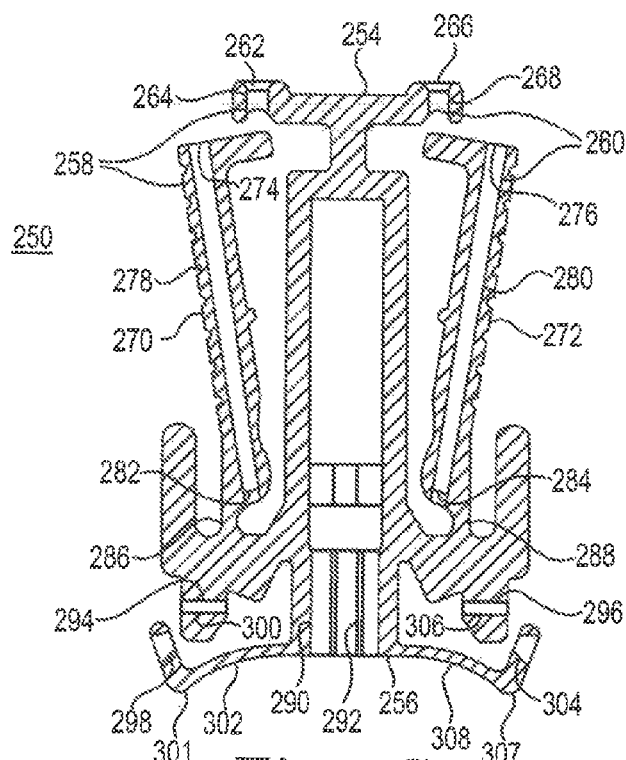
Figure 6D:
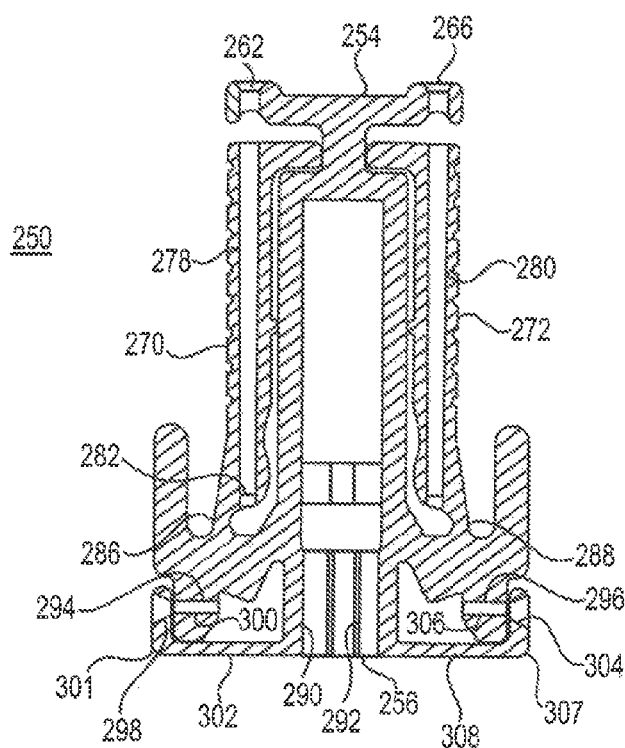

FIGS. 6A-6E illustrate a temporary touch-proof connector 250 similar to touch-proof connector 200 illustrated in FIGS. 5A-5D. Touch-proof connector 250 is formed of a connector body 252 having a first end 254, a second end 256 and first and second passageways 258 and 260. First end 254 includes a first opening 262 leading to a passageway segment 264 of passageway 258 and a second opening 266 leading to a passageway segment 268 of passageway 260. Connector 250 also includes locking portions 270 and 272 that include corresponding openings 274 and 276, respectively. Openings 274 and 276 lead to passageway segments 278 and 280, respectively. Passageways 258 and 260 terminate at enclosed ends 282 and 284, respectively. Locking portions 270 and 272 are coupled to connector body 252 through flexing portions 286 and 288, respectively. During use, locking portions 270 and 272 are compressed (i.e., pushed together toward each other) such that passageway segments 278 and 280 are generally aligned with passageway segments 264 and 268, respectively, as shown in FIG. 6D. Once aligned, connector elements can be inserted through openings 262 and 266 and into passageway segments 270 and 272. As a result, multiple connecting elements can be positioned within connector 250.

When used as a carrier during packaging and distribution, touch-proof connector 250 includes internal passageways 290 and 292 that are configured to receive needles (e.g., needle 12) therein. As such, these needles will be protected during packaging and distribution. Additionally, connector 250 includes a first lower passageway 294 and a second lower passageway 296, configured to secure atraumatic curved needles (e.g., needle 90) therein. In the embodiment illustrated, passageways 294 and 296 are oriented generally perpendicular to passageways 258 and 260, when connector 250 is in the open configuration shown in FIG. 6D.

Passageway 294 includes a first passageway segment 298 configured to be aligned with a second passageway segment 300. Passageway segment 298 is formed in a locking portion 301 that is connected to connector body through a flexing portion 302. During packaging, locking portion 301 can be actuated such that passageway segments 298 and 300 are aligned, as shown in FIG. 6D. Once aligned, an atraumatic needle (e.g., needle 90) is inserted into passageway segments 298 and 300. Upon release of locking portion 301, needle 90 is secured therein and thus is protected during packaging and distribution. Passageway 296 is similar to passageway 294 and defines a first passageway segment 304 and a second passageway segment 306. First passageway segment 304 is formed in a locking portion 307. Locking portion 307 can be actuated such that passageway segment 304 is generally aligned with a passageway segment 306. Additionally, locking portion 307 is connected to connector body through a flexing portion 308. During packaging, locking portion 307 can be actuated such that passageway segments 304 and 306 are generally aligned. An atraumatic needle (e.g., needle 90), can then be inserted into passageway segments 304 and 306 for protection during packaging and distribution.

Figure 6E:
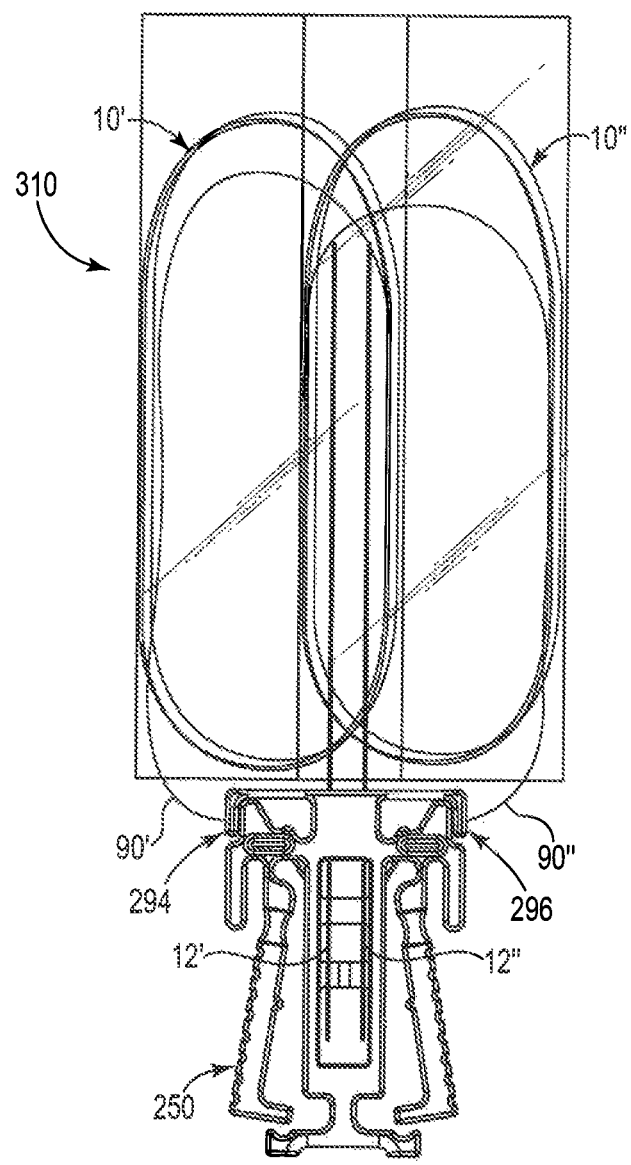

As illustrated in FIG. 6E, a sterilized package 310 can be utilized to package and distribute leads 10' and 10'' illustrated in FIG. 6E. As shown in FIG. 6E, needle 12' of lead 10' has been inserted into connector 250 (e.g., within passageway 290) whereas needle 12'' of lead 10'' has been inserted into connector 250 (e.g., within passageway 292). Additionally, atraumatic needle 90' is inserted and secured within passageway 294 whereas atraumatic needle 90'' of lead 10'' is secured within passageway 296. As such, package 310 can be distributed safely without any of the needles (12', 12'', 90', 90'') ripping or tearing the packaging 310. Moreover, a user receiving package 310 may easily inspect each of the needles for damage thereto before opening and/or using the leads 10' and 10''

Figure 7A:
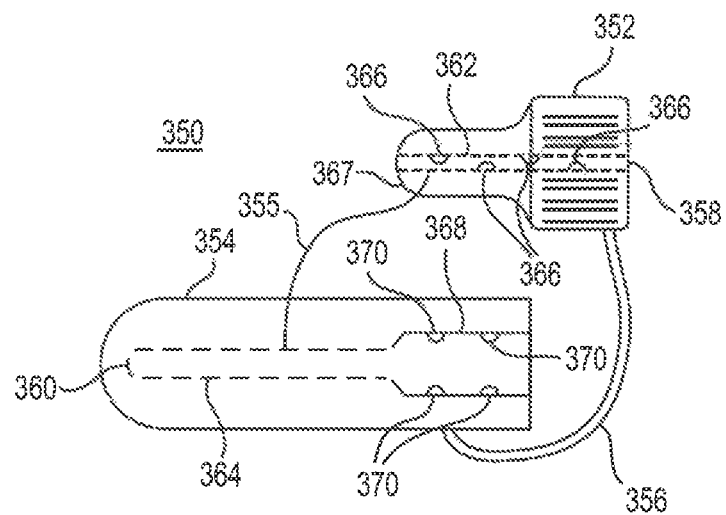
FIGS. 7A-7C illustrate various views of a sixth embodiment of a temporary touch-proof connector.
Figure 7B:
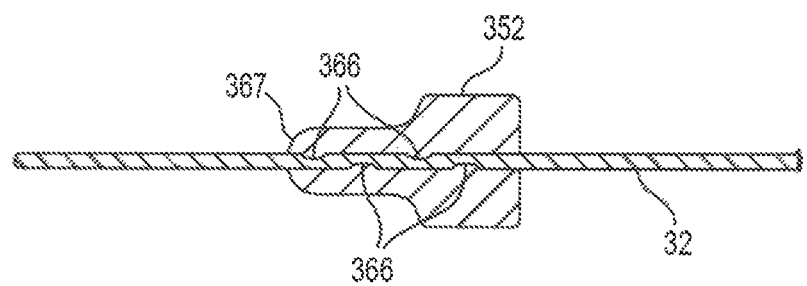
Figure 7C:
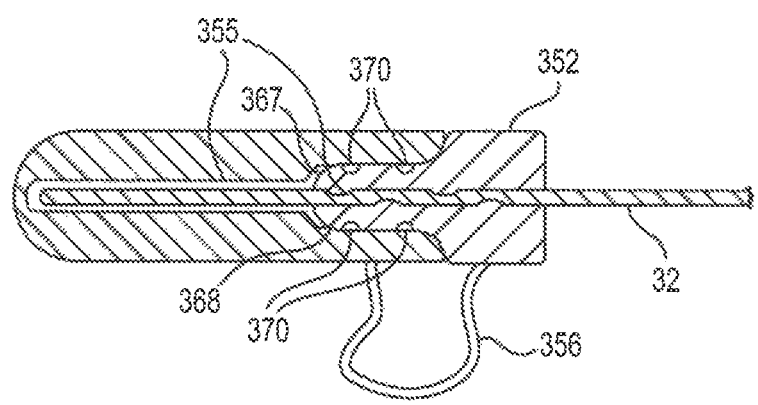

FIGS. 7A-7C illustrate a connector 350 formed of a gripping portion 352 and a cap 354 connected together via a cord or lanyard 356. Together, gripping portion 352 and cap 354 form a passageway 355 including an open, leading end 358 and a trailing enclosed end 360. The passageway 355 is formed of a first passageway segment 362 maintained within gripping portion 352 and a second passageway segment 364 maintained within cap 354. Segment 362 includes a plurality of projections 366 that engage the connector element 32 and prevents the connector element 32 from sliding with respect to the segment 362. Gripping portion 352 includes a tapered end 367 configured to be positioned within a corresponding receiving portion 368 of cap 354. A plurality of projections 370 are provided in receiving portion 368 to interface with tapered end 367. During use, connector element 32 is inserted through segment 362 and into passageway segment 364 to shield the connector element 32. To use connector element 32, cap 354 is removed from gripping portion 352 as shown in FIG. 7B such that connector element 32 is exposed and can be connected to a pacemaker. When not in use, gripping portion 252 is inserted into receiving portion 268 to protect connecting element 32.

Figure 8A:
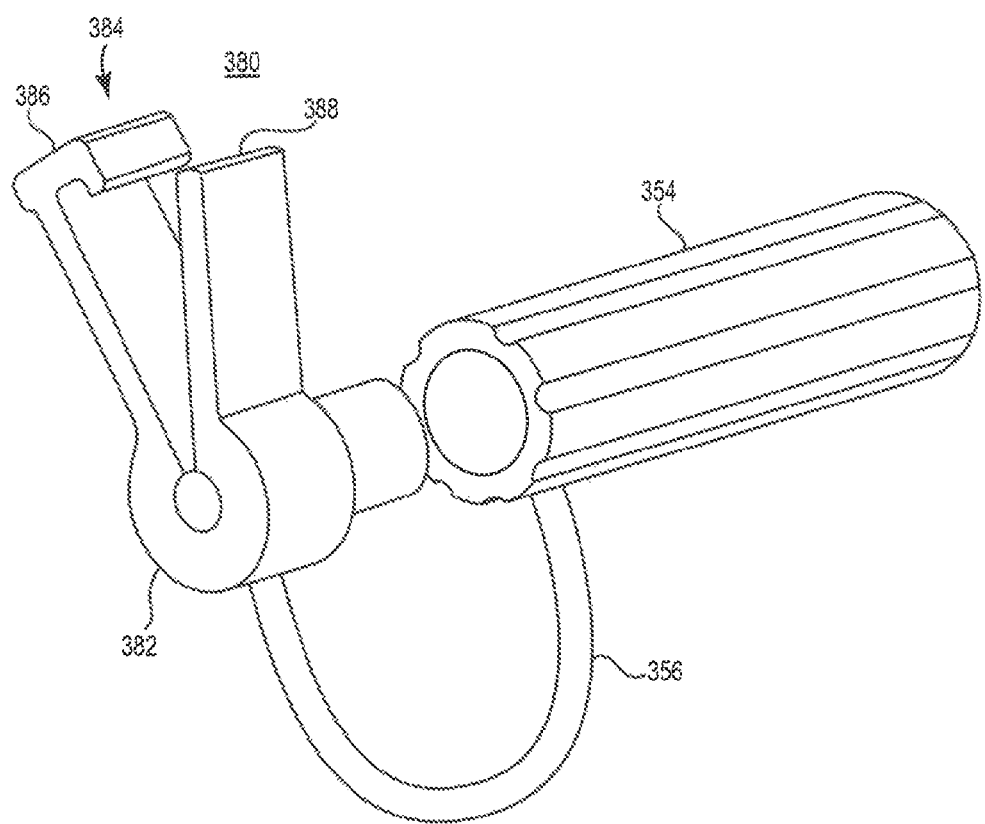
FIGS. 8A-8D illustrate various view of a seventh embodiment of a temporary touch-proof connector.
Figure 8B:
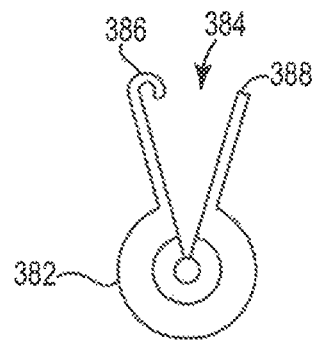
Figure 8C:
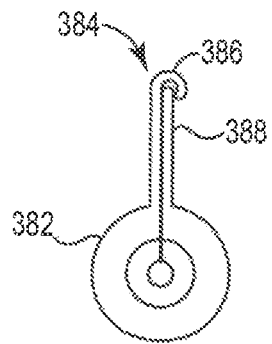
Figure 8D:
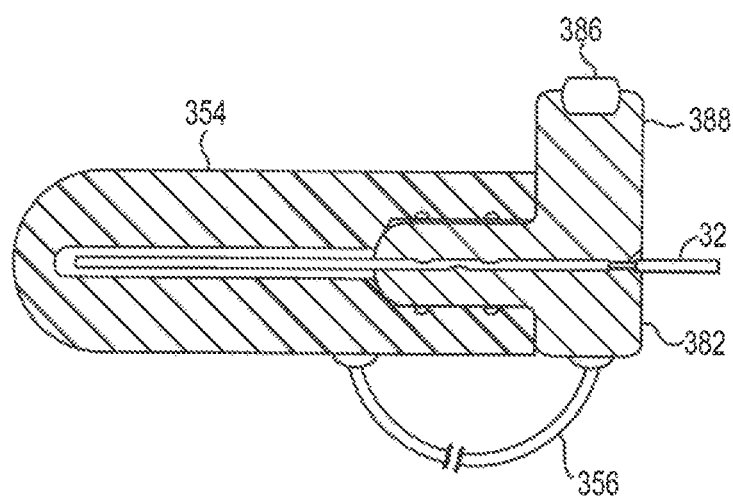

FIGS. 8A-8D illustrate a connector 380 similar to connector 350 shown in FIGS. 7A-7C, having a similar cap 354 and an alternative gripping portion 382 connected together by lanyard 356. Gripping portion 382 includes a clamping mechanism 384 formed of a hook portion 386 and a hook receiving portion 388. The connector element 32 is inserted within clamping mechanism 384 and hook portion 386 is slid over a receiving portion 388 to a locked position so as to secure connector element 32 therebetween. Gripping portion 382 can then be positioned within cap 354 similar to that shown in FIGS. 7A-7C and as illustrated in FIG. 8D.

Although the present disclosure has been described with reference to preferred embodiments, workers skilled in the art will recognize that changes can be made in form and detail without departing from the spirit and scope of the present disclosure.

What is claimed is:

1. A method of coupling a temporary touch-proof connector with a connector element of a lead, comprising:
    providing an insulating body;
    providing a passageway in the insulating body defining an open leading end and an enclosed trailing end, the passageway formed of an insulating material;
    transitioning the passageway to an open configuration by deforming the insulating body to alter a shape of the passageway;
    inserting the connector element within the passageway so as to prevent electrical current or static electricity from passing through the lead external the insulating body; and
    transitioning the passageway to a closed configuration by releasing the insulating body to secure the connector element within the passageway.

2. The method of claim 1, wherein the deforming further comprises altering a cross sectional shape of the passageway from an elliptical shape to a circular shape.

3. The method of claim 1, wherein the deforming further comprises aligning a first passageway segment and a second passageway segment.

4. The method of claim 1, further comprising:
providing a first passageway segment and a second passageway segment associated with the passageway;
aligning the first passageway segment and the second passageway segment; and
inserting the connector element into the first passageway segment and the second passageway segment.

5. The method of claim 4, wherein the second passageway segment is positioned in a locking portion that is coupled to the insulating body by a flexing portion.

6. The method of claim 4, further comprising:
providing a second passageway in the insulating body, the second passageway including a third passageway segment and a fourth passageway segment;
aligning the third passageway segment and the fourth passageway segment; and
inserting a second connector element into the third passageway segment and the fourth passageway segment.

7. The method of claim 6, further comprising:
positioning a third passageway and a fourth passageway in the insulating body between the passageway and the second passageway.

8. The method of claim 6, further comprising:
providing a third passageway in the insulating body, the third passageway including a fifth passageway segment and a sixth passageway segment;
aligning the fifth passageway segment and the sixth passageway segment; and
inserting a needle into the fifth passageway segment and the sixth passageway segment.

9. A temporary touch-proof connector for securing a connector element of a lead, comprising:
an insulating body; and
a passageway formed of insulating material and defining an open leading end and an enclosed trailing end, the passageway positioned within the insulating body and configured to be transitioned between an open configuration by deforming the insulating body to alter a shape of the passageway such that a connector element is received within the passageway and a closed configuration by releasing the insulating body to secure the connector element within the passageway so as to prevent electrical current or static electricity from passing through the lead external the insulating body.

10. The connector of claim 9, wherein the passageway includes a minor axis, the minor axis forms a first shape in the open configuration, the first shape being a greater size than the diameter of the connector element, further wherein the minor axis forms a second shape in the closed configuration, the second shape being a smaller size than a diameter of the connector element.

11. The connector of claim 10, wherein the insulating body is biased to the closed configuration.

12. The connector of claim 11, wherein the first shape is a circular cross-section and wherein the second shape is an elliptical cross-section.

13. The connector of claim 9, wherein the passageway includes a first passageway segment and a second passageway segment, wherein in the open configuration, the first passageway segment and the second passageway segment are aligned.

14. The connector of claim 13, wherein the second passageway segment is positioned in a locking portion that is pivotally coupled to the insulating body.

15. The connector of claim 13, further comprising:
a second passageway positioned within the insulating body, the second passageway including a third passageway segment and a fourth passageway segment.

16. The connector of claim 15, wherein the second passageway is configured to transition between an open configuration, wherein the third passageway segment and the fourth passageway segment are generally aligned and a closed configuration, wherein the third passageway segment and the fourth passageway segment are not aligned.

17. The connector of claim 16, further comprising:
a third passageway positioned in the insulating body between the passageway and the second passageway; and
a fourth passageway positioned in the insulating body between the passageway and the second passageway.

18. The connector of claim 16, further comprising:
a third passageway positioned in the insulating body, the third passageway including a fifth passageway segment and a sixth passageway segment, the third passageway configured to transition from an open configuration, wherein the fifth passageway segment and the sixth passageway segment are aligned and a closed configuration.

19. The connector of claim 9, wherein the passageway in the closed configuration comprises a leading straight segment adjacent the open leading end, a trailing straight segment adjacent the enclosed trailing end, and an intermediate arcuate segment disposed between the leading straight segment and the trailing straight segment.

20. The connector of claim 19, wherein the passageway in the open configuration is deformed such that the intermediate segment is aligned with the leading straight segment and the trailing straight segment.

21. A temporary touch-proof connector for securing a connector element of a lead, comprising:
an insulating body; and
a passageway formed of insulating material and defining an open leading end and an enclosed trailing end, the passageway positioned within the insulating body and includes a first passageway segment and a second passageway segment associated with the passageway, wherein the first and second passageway segments are offset from one another and the passageway is defined when the first and second passageway segments are aligned by deforming the insulating body such that a connector element is received within the first and second passageways to secure the connector element within the first and second passageways so as to prevent electrical current or static electricity from passing through the lead external the insulating body.

22. The connector of claim 21, wherein the second passageway segment is positioned in a locking portion that is coupled to the insulating body by a flexing portion.

* * * * *